(12) United States Patent
Arramon et al.

(10) Patent No.: US 9,943,416 B2
(45) Date of Patent: *Apr. 17, 2018

(54) INTERVERTEBRAL SPACER THAT DYNAMICALLY PROMOTES BONE GROWTH

(71) Applicant: Simplify Medical Pty Limited, Toronto (CA)

(72) Inventors: Yves Arramon, Sunnyvale, CA (US); David Hovda, Mountain View, CA (US)

(73) Assignee: Simplify Medical Pty Limited (AU)

( * ) Notice: Subject to any disclaimer, the term of this patent is extended or adjusted under 35 U.S.C. 154(b) by 268 days.

This patent is subject to a terminal disclaimer.

(21) Appl. No.: 15/065,774

(22) Filed: Mar. 9, 2016

(65) Prior Publication Data

US 2016/0262908 A1 Sep. 15, 2016

Related U.S. Application Data

(60) Provisional application No. 62/131,154, filed on Mar. 10, 2015.

(51) Int. Cl.
*A61F 2/44* (2006.01)
*A61F 2/46* (2006.01)
(Continued)

(52) U.S. Cl.
CPC ............ *A61F 2/4455* (2013.01); *A61F 2/447* (2013.01); *A61F 2/4465* (2013.01); *A61F 2/4611* (2013.01); *A61B 17/7059* (2013.01); *A61F 2002/302* (2013.01); *A61F 2002/3008* (2013.01); *A61F 2002/30014* (2013.01); *A61F 2002/30028* (2013.01); *A61F 2002/3093* (2013.01); *A61F 2002/3097* (2013.01); *A61F 2002/30131* (2013.01); *A61F 2002/30135* (2013.01); *A61F 2002/30158* (2013.01); *A61F 2002/30563* (2013.01); *A61F 2002/30622* (2013.01); *A61F 2002/30782* (2013.01); *A61F 2002/30968* (2013.01); *A61F 2002/4475* (2013.01); *A61F 2220/0016* (2013.01);
(Continued)

(58) Field of Classification Search
CPC ..... A61F 2/4465; A61F 2/4611; A61F 2/4455
See application file for complete search history.

(56) References Cited

U.S. PATENT DOCUMENTS 6,395,033 B1    5/2002   Pepper
6,652,592 B1   11/2003   Grooms et al.
(Continued)

FOREIGN PATENT DOCUMENTS

WO    WO-2016145180 A1    9/2016

OTHER PUBLICATIONS

U.S. Appl. No. 15/212,154, filed Sep. 15, 2016, Arramon et al.
(Continued)

*Primary Examiner* — Christian Sevilla
(74) *Attorney, Agent, or Firm* — Wilson Sonsini Goodrich & Rosati

(57) ABSTRACT

A dynamic intervertebral spacer includes a ring which is split on an anterior portion. A posterior portion of the ring acts as a torsion spring. After implantation, the ring is able to act as a spring between superior and inferior vertebral bodies, thus allowing dynamic bone growth in fusion procedures.

22 Claims, 8 Drawing Sheets

(51) Int. Cl.
*A61F 2/30* (2006.01)
*A61B 17/70* (2006.01)

(52) U.S. Cl.
CPC ............... *A61F 2310/00023* (2013.01); *A61F 2310/00029* (2013.01); *A61F 2310/00059* (2013.01); *A61F 2310/00101* (2013.01); *A61F 2310/00131* (2013.01)

(56) References Cited

U.S. PATENT DOCUMENTS

| | | |
|---|---|---|
| 7,618,458 B2 | 11/2009 | Biedermann et al. |
| 7,666,226 B2 * | 2/2010 | Schaller ................ A61B 17/70 623/17.11 |
| 7,794,502 B2 | 9/2010 | Michelson |
| 7,947,078 B2 | 5/2011 | Siegal |
| 8,685,101 B2 | 4/2014 | Kraft et al. |
| 2008/0183293 A1 | 7/2008 | Parry et al. |
| 2009/0093885 A1 | 4/2009 | Levieux et al. |
| 2009/0192617 A1 | 7/2009 | Arramon et al. |
| 2010/0312346 A1 | 12/2010 | Kueenzi et al. |
| 2011/0166656 A1 | 7/2011 | Thalgott et al. |
| 2011/0245926 A1 * | 10/2011 | Kitchen ................ A61F 2/4465 623/17.16 |
| 2013/0253650 A1 | 9/2013 | Ashley et al. |
| 2013/0296940 A1 | 11/2013 | Northcutt et al. |
| 2013/0345814 A1 | 12/2013 | Walkenhorst et al. |
| 2014/0052258 A1 | 2/2014 | Ball et al. |
| 2016/0324658 A1 | 11/2016 | Arramon et al. |

OTHER PUBLICATIONS

International search report and written opinion dated Jun. 24, 2016 for PCT/US2016/021747.
Co-pending U.S. Appl. No. 15/673,294, filed Aug. 9, 2017.
Extended European search report and opinion dated Aug. 10, 2017 for EP Application No. 16724840.
Office action dated Jun. 21, 2017 for U.S. Appl. No. 15/212,154.
Office action dated Jan. 18, 2017 for U.S. Appl. No. 15/212,154.

* cited by examiner

INTERVERTEBRAL SPACER THAT DYNAMICALLY PROMOTES BONE GROWTH

CROSS-REFERENCE TO RELATED APPLICATIONS

This application claims the benefit of provisional application No. 62/131,154, filed on Mar. 10, 2015, the full disclosure of which is incorporated herein by reference.

BACKGROUND OF THE INVENTION

1. Field of the Invention

The present invention relates to medical devices and methods. More specifically, the invention relates to intervertebral spacers methods for dynamically promoting bone growth and fusion following implantation of the spacer.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

When a damaged intervertebral disc causes a patient pain and discomfort, surgery is often required. Typically, surgical procedures for treating intervertebral discs involve discectomy (partial or total removal of a disc), often followed by interbody fusion of the superior and inferior vertebrae adjacent to the disc. Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together.

While such fusion procedures have been very successful for many patients, it some cases the fusion spacers or cages can be difficult to implant, and the bone regrowth necessary to achieve complete fusion can take an excessive period of time. Therefore, a need exists for an improved spacers and methods for fusing the spacers to promote complete and rapid bone regrowth. At least some of these objectives will be met by the inventions described herein below.

2. Description of the Background Art

A compliant block intended to be implanted between adjacent vertebrae to promote fusion as described in U.S. Pat. No. 6,395,033. Partially compliant fusion cages and spacers are described in U.S. Pat. No. 8,685,101 and U.S. Pat. Publ 2009-0093885. An interspinous fusion device which dynamically promotes bone growth is described in U.S. Pat. Publ. 2013-0296940. Flexible devices which may be coiled and implanted between vertebrae are described in U.S. Pat. Nos. 7,666,226 and 7,947,078. A bone implant that may have a U-shape is described in U.S. Pat. No. 6,652,592.

BRIEF SUMMARY OF THE INVENTION

The present invention provides alternative and improved apparatus and methods for performing interbody spinal fusion procedures. In particular, improved fusion spacers are provided which are relatively compact and simple to implant. The fusion cages are configured not only to fill the space between adjacent superior and inferior vertebrae after disc removal, they also provide for a compliant support which allows relative movement between the superior and inferior vertebrae as the patient moves about and the patient's spine undergoes flexion and extension. The spacers have very simple designs, are easy to manufacture, and provide for rapid attachment to the superior and inferior vertebral bodies while continuing to allow the desired relative motion of the vertebral bodies to dynamically promote bone growth.

In a first aspect, the present invention provides a dynamic intervertebral spacer. The spacer comprises a ring having an anterior portion, a posterior portion, a right lateral portion, a left lateral portion, and an open center portion, wherein the ring is configured to be implanted between an adjacent superior vertebral body and an adjacent inferior vertebral body, typically following a discectomy procedure. The ring is split in the anterior portion, and superior and inferior surfaces on a right side thereof are vertically offset from superior and inferior surfaces on a left side thereof. The posterior portion of the ring is configured to act as a torsion spring to allow the vertical offset between the right side and left side of the ring to decrease under load on the superior and inferior surfaces of the ring. When the adjacent vertebral bodies between which the spacers implanted are under minimal load, the offset will be maximum, and conversely when the adjacent vertebral bodies apply a maximum load (compressive force) to the spacer, the vertical offset will be minimum. Thus, as the load increases and decreases, the spacing between the vertebral bodies will decrease and increase, respectively. Such dynamic loading has been found to promote tissue growth, particularly when bone graft materials were placed within the open center portion of the ring.

In exemplary embodiments, one of the superior and inferior surfaces on the right side of the ring (but not the other) will have attachment features or adhesives which provide for attachment to an adjacent vertebral body and one of the superior and inferior surfaces on the left side (but not the other) will have attachment features or adhesives which provide for attachment to an adjacent vertebral body. By arranging the attachment features on opposite surfaces, i.e. one will be on a superior surface and one will be on an inferior surface, a vertically raised superior surface one side of the ring will be attached to the superior vertebral body while a vertically lowered inferior surface on the other side of the ring will be attached to the inferior vertebral body. Usually, the surfaces on the superior and inferior faces of the ring which contact the bone will have features, coatings, or the like which promote bone ingrowth. In contrast, the surfaces on the ring which are intended to remain out of contact with the adjacent vertebral bodies will be free from such bone growth promoting and coatings. Alternatively or additionally, the right and left sides of the ring may each have at least one bone screw, with a bone screw on one side is configured to attach to a posterior vertebral body and the bone screw on the other side of the ring is configured to attach to an inferior vertebral body. Some instances, more than one bone screw may be used on each side of the ring.

The manner in which the ring is split on the interior surface may take a variety of forms or geometries. In an exemplary geometry, terminal faces on the right and left sides of a gap in the anterior portion of the ring will each be flat, and optionally vertical. In other instances, the opposed faces may be non-planar. Such non-planar surfaces may define separation paths which are non-linear in either a superior-to-inferior direction or in an anterior-to-posterior direction. Such non-linear separation paths may be advantageous in that they help retain the bone graft material within the open center portion of the ring.

In other specific embodiments, the ring consists of a monolithic body. Such monolithic bodies may be formed by casting, molding, machining, or the like, and will be free from joints and other non-continuous regions. The monolithic bodies may be formed from a polymer, such as a poly ether ketones (PEEK), polyaryl ether ketones (PAEK), and their composites, such as carbon fiber reinforced or with radiopaque compounds. In still other instances, the monolithic body may consist of a metal. Exemplary metals, include tantalum or titanium, and their alloys and composites such as nitinol, cobalt chrome molybdenum and variants. In addition, the metals may be either porous for the purpose of adjusting the bulk stiffness of the material, or for enhancing osteo-integration. The different metal morphologies may be a result of additive manufacturing, such as direct metal laser-sintering or vacuum sintering.

The vertical offset will typically be in the range of 0.05 mm to 3.0 mm, often from 0.1 mm to 1.75 mm, and usually from 0.2 mm to 1.0 mm. The offsets in the lumbar spine will typically be at the higher ends of this range while those in the thoracic spine will be toward the middle or lower middle and those in the cervical spine will be in the lower portion of the offset. The material and structure of the ring will usually be selected so that the vertical offset resists compression with a spring force in the range from 20 N/mm to 40000 N/mm, usually from 150 N/mm to 5000 N/mm, and typically from 250 N/mm to 1000 N/mm. In still further specific embodiments, the superior surface of the spacer may have a convex or "domed" geometry.

In a second aspect in the present invention, a method for dynamically fusing adjacent vertebral bodies in a patient's spine comprises implanting a spacer between the adjacent vertical bodies (typically after a discectomy or other procedure to remove the native disc). An open center of the spacer is filled with a bone graft material, and the superior and inferior surfaces on a right side of an anterior portion of the spacer are vertically offset from the superior and inferior surface on the left side of the anterior portion of the spacer. The spacer is configured so that the vertical offset elastically resists flexion as the patient's spine goes through flexion and extension, or the resistance to flexion dynamically promotes bone growth.

The vertical offset typically has a magnitude in the ranges set forth above and resists flexion with an elastic constant in the ranges set forth above. The vertical offset is typically formed by a space or gap between the superior surface and the adjacent vertebral body on one side of the spacer and a gap or space between the inferior surface and the other adjacent vertebral body on the other side of the spacer. These gaps in turn allow the free surfaces of the spacer (which are not attached to a vertebral body) to move toward and away from the adjacent vertebral bodies to allow the desired dynamic motion between those vertebral bodies. Typically, the surfaces on the spacer which are normally in contact with the adjacent vertebral body surfaces will be attached to those vertebral body surfaces, in some way. For example, bone screws may be used to attach the surfaces. Alternatively, bone growth promoting features or coatings may be placed on those portions of the superior and inferior surfaces of the spacer which are intended to be in contact with the adjacent vertebral bodies. Those surface portions which are intended to not be in contact with the vertebral bodies will of course be free of such bone attachment features.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows the dynamic intervertebral spacer oriented with the anterior portion downward to expose the superior surface of the spacer. FIG. 1B is a front or anterior elevation view showing the vertical offset of the right and left sides of the spacer.

FIG. 5A is a view of the anterior side of the spacer while FIGS. 5B and 5C are views of the inferior and superior surfaces, respectively.

DETAILED DESCRIPTION OF THE INVENTION

Figure 1A:
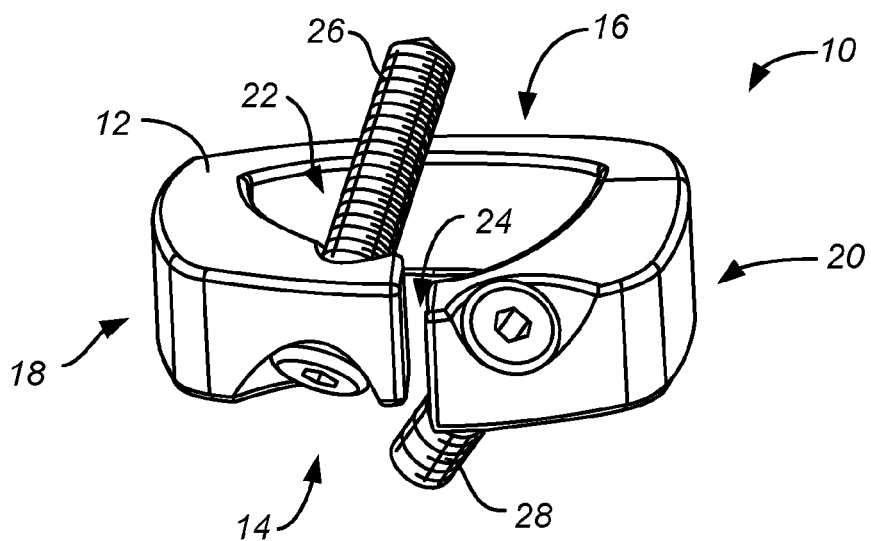
FIGS. 1A and 1B illustrate a first embodiment of a dynamic intervertebral spacer constructed in accordance with the principles of the present invention.
Figure 1B:
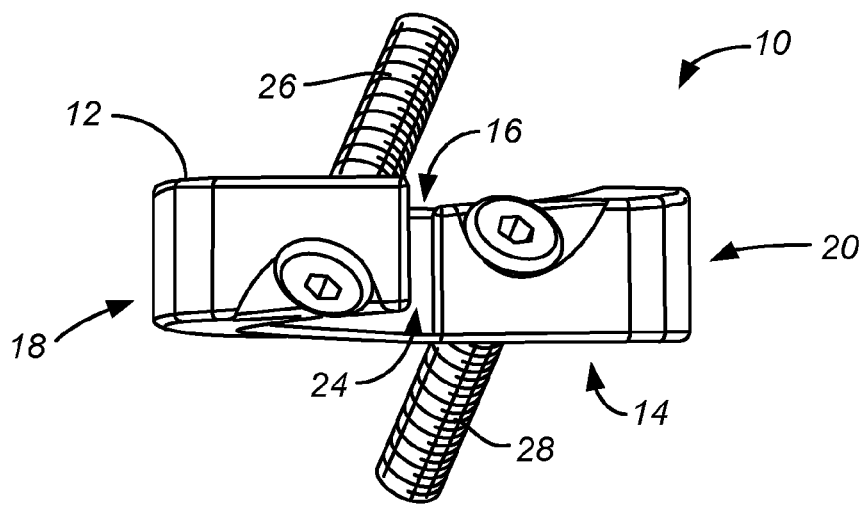

Referring to FIGS. 1A and 1B, a dynamic intervertebral spacer 10 comprises a ring 12 (which forms a body thereof) having an anterior portion 14, a posterior portion 16, a right lateral portion 18, a left lateral 20, and an open center 22. The ring as illustrated has four sides with the posterior portion 16 being slightly wider than the anterior portion 14. The ring will also have a depth in a horizontal or anterior-posterior direction and a thickness in the vertical or superior-inferior direction. Representative dimensions for the exemplary ring for each of three intended implantation locations (lumbar, thoracic, and cervical) are set forth in Table I below.

TABLE I

| | Anterior Width | Posterior Width | Depth | Thickness | Vertical Offset |
| --- | --- | --- | --- | --- | --- |
| LUMBAR | 30-50 mm | 25-45 mm | 25-40 mm | 8-15 mm | 0.1-3 mm |
| THORACIC | 23-36 mm | 15-29 mm | 17-30 mm | 4-9 mm | 0.1-2.5 mm |
| CERVICAL | 14-20 mm | 14-20 mm | 3-8 mm | 3-8 mm | 0.1-1.75 mm |

The specific geometry and dimensions set forth above are not critical and are meant to be exemplary only. Other geometries, such as circular, oval, triangular, rectangular, polygonal, and the like, may also find use. In all cases, however, there will be at least one break in the ring to form a gap 24 between opposed free ends of the ring. The free ends of the ring will be vertically offset by a small distance, typically in the ranges set forth above in the Summary, in order to allow the spacer to act as a "spring" when implanted between a lower surface of a superior vertebral body and an upper surface of an inferior vertebral body, will be described in more detail below. Representative vertical offsets are provided in Table 1 for each of the different implantation regions.

Figure 2A:
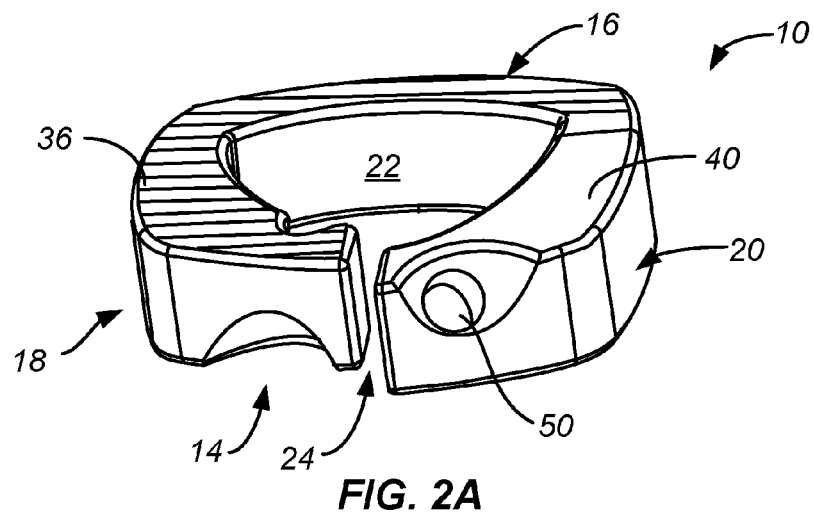
FIGS. 2A through 2C are alternative views of the dynamic intervertebral spacer of FIGS. 1A and 1B shown with the bone anchoring screws removed.
Figure 2B:
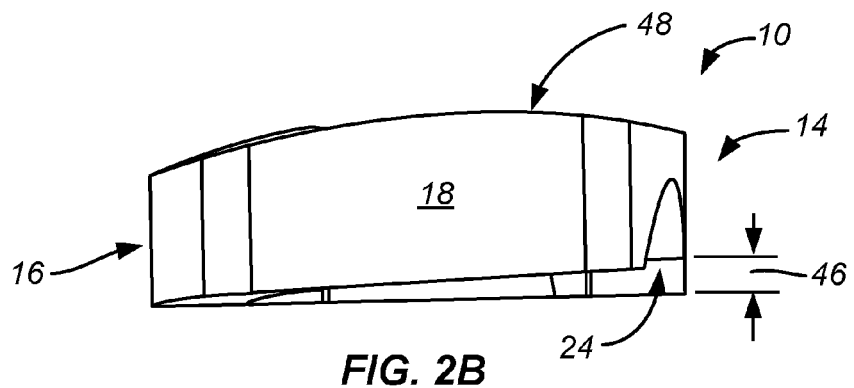
Figure 2C:
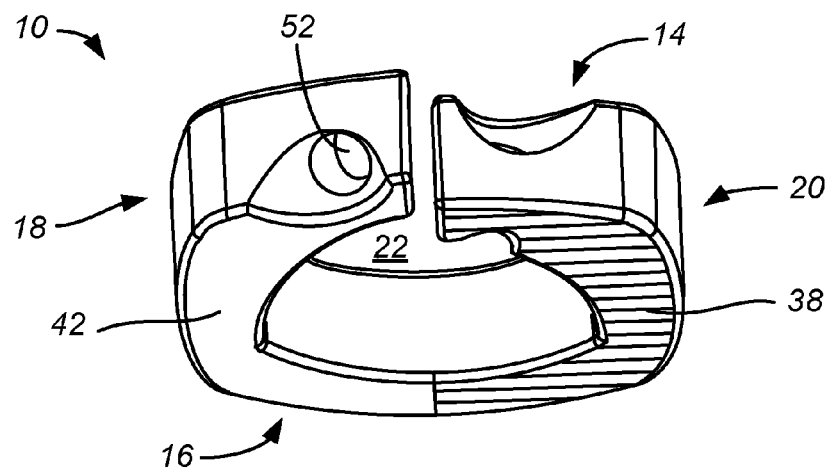

Referring now to FIGS. 2A through 2C, the ring 12 of the dynamic intervertebral spacer 10 may optionally be modified to promote bone ingrowth over certain selected regions thereof. As shown in FIGS. 2A and 2C, a superior bone attachment region 36 may be formed over the right lateral portion 18 and over a right side of the posterior portion 16 of the device. It will be appreciated that these attachment regions on the superior surface are elevated relative to the superior surface left lateral portion 20 and will be in contact with the lower surface of the superior vertebral body when the spacer is implanted. The surface modifications may be features, such as ridges, grooves, and the like, or may alternatively comprise coatings selected to promote bone ingrowth, such as titanium plasma spray or hydroxyapetite. The surface modifications will be in addition to, or in some cases in place of, use of a superior bone attachment screw 26 which is received in an inferior screw hole 52 in the anterior portion of the right lateral portion 18 of the ring.

An inferior bone attachment region 38 will typically be formed over the inferior surface of the left lateral portion 20 of the ring 12, as shown in FIG. 2C. The inferior bone attachment region will typically have the same characteristics as the superior bone attachment region 36, and may be used together with or in place of an inferior bone attachment screw 28 which is received through the superior screw hole 50 on an anterior region of the left lateral portion 20.

Referring specifically to FIG. 2B, the right lateral portion 18 and the left lateral portion 20 of the ring 12 are vertically offset to create an offset 46, as best seen in FIG. 2B. Exemplary vertical offsets are set forth in Table I above. It is this differential or offset which allows the ring 12 to act as a spring when implanted between superior and inferior vertebral bodies. In the particular ring design 12, the bending or spring constant of the ring will be defined by the torsional stiffness of the posterior portion 16. That is, the right lateral portion 18 and left lateral portion 20 will act as bending arms connected to the posterior portion 16, were the posterior portion acts as a torsional spring. Particular spring constants have been set forth above.

Figure 3A:
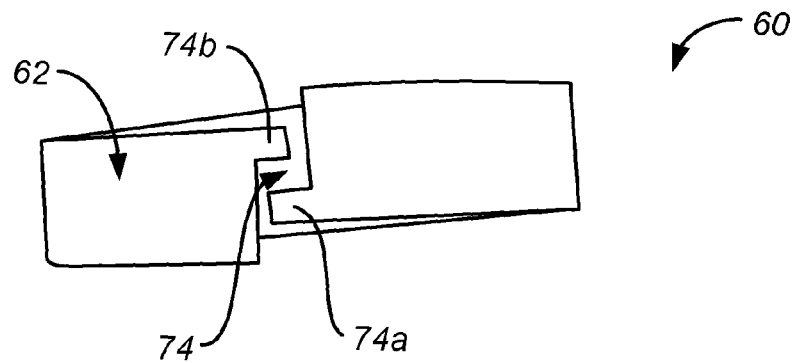
FIGS. 3A and 3B illustrate a first alternative design of a dynamic intervertebral spacer of the present invention.
Figure 3B:
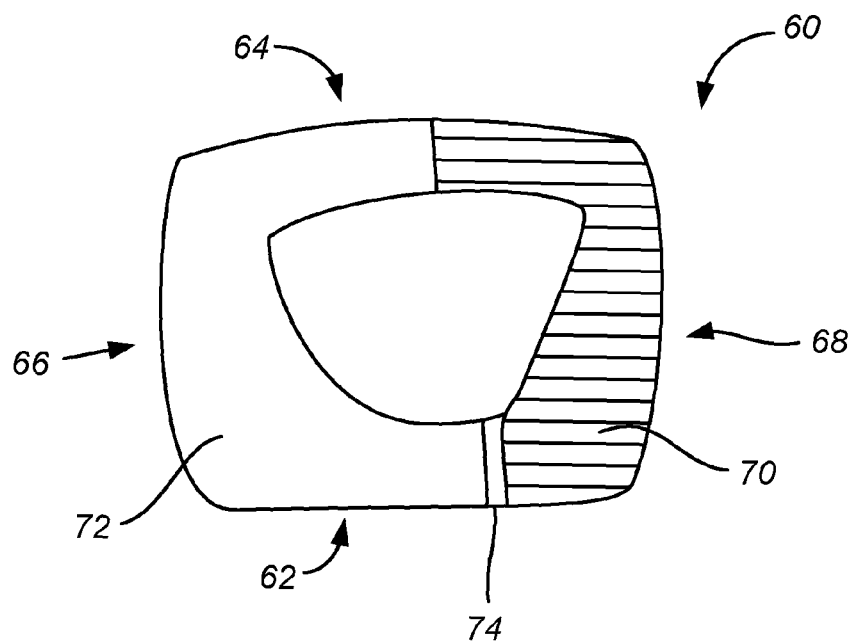

Referring now to FIGS. 3A and 3B, the gap between the right lateral portion and left lateral portion of the intervertebral spacer of the present invention may take a variety of forms and geometries. In an alternative ring construction 60 of FIGS. 3A and 3B, a right lateral portion 66 and left lateral portion 68 of the ring have a gap 74 which is linear in the anterior-posterior direction but non-linear in the superior-inferior direction. In particular, the gap 74 is defined by an inferior tab 74a and a superior tab 74b which together form an opening which has two vertical portions joined by a horizontal portion. The right lateral portion 66 and left lateral portion 68 are vertically offset relative to each other, where the degree of vertical offset is limited by the tabs which will in turn also limit the degree of extension to prevent excessive extension. The ring 60 will also have an anterior portion 62, a posterior portion 64, and a superior bone attachment region 70 having any of the characteristics previously described as well as a superior region 72 which is free from any bone attachment features. Although not illustrated, the ring 60 will typically also be configured to receive bone attachment screws, and the inferior surface of the ring will also have a bone attachment region on the right lateral portion and region free from bone attachment features on the left lateral portion.

Figure 4A:
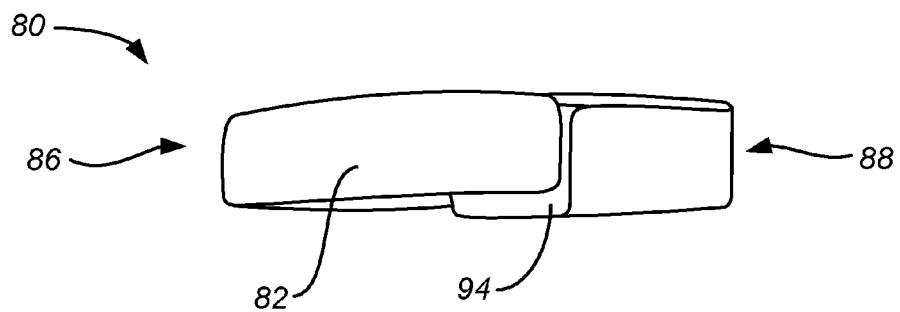
FIGS. 4A and 4B illustrate a second alternative design for an intervertebral spacer of the present invention.
Figure 4B:
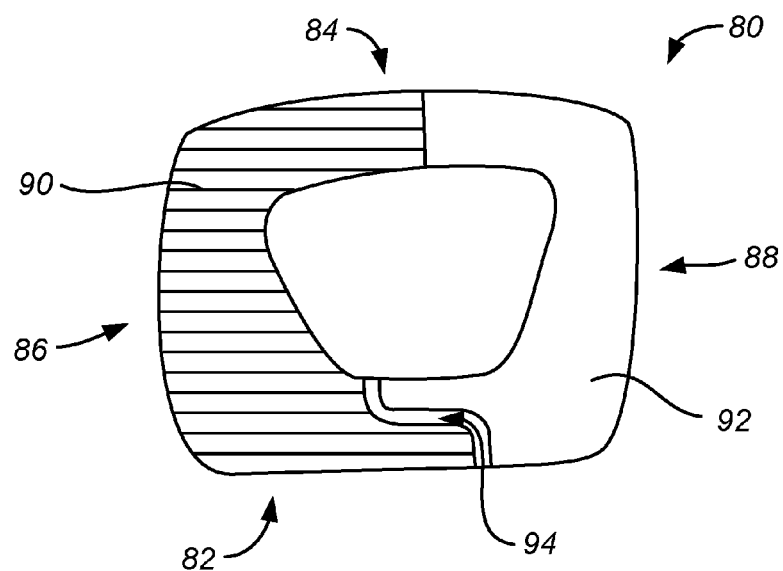

Referring now to FIGS. 4A and 4B, a further alternative ring 80 is similar to the previously described embodiments, but includes a gap region 94 which is linear in the superior to inferior direction and non-linear in the anterior to posterior direction. Particular, the ring 80 has an anterior portion 82, a posterior portion 84, a right lateral portion 86, and a left lateral portion 88. A superior bone attachment region 90 is formed over the right lateral portion 86 which is raised relative to the left lateral portion 88. A superior surface 92 of the left lateral portion 88 is free from bone detachment features. The gap 94 is shown to include two axial lengths in the anterior-to-posterior direction joined by a lateral length in the lateral direction. The use of non-linear gap regions is advantageous as in can help retain the bone graft material in the open centers of the rings.

Figure 5A:
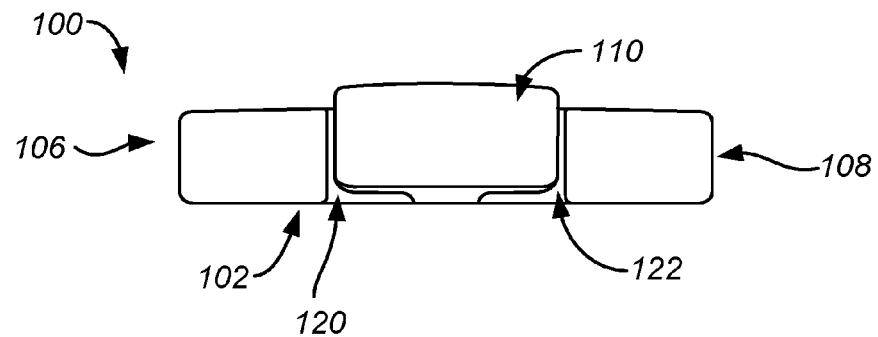
FIGS. 5A-5C illustrate a second alternative design for an intervertebral spacer of the present invention.
Figure 5B:
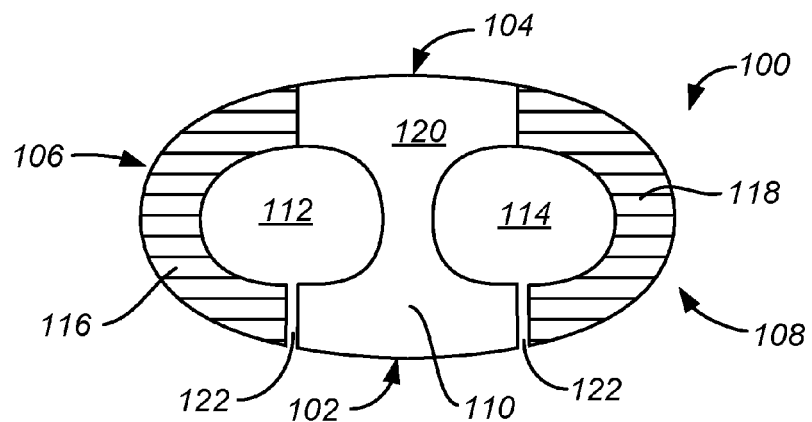
Figure 5C:
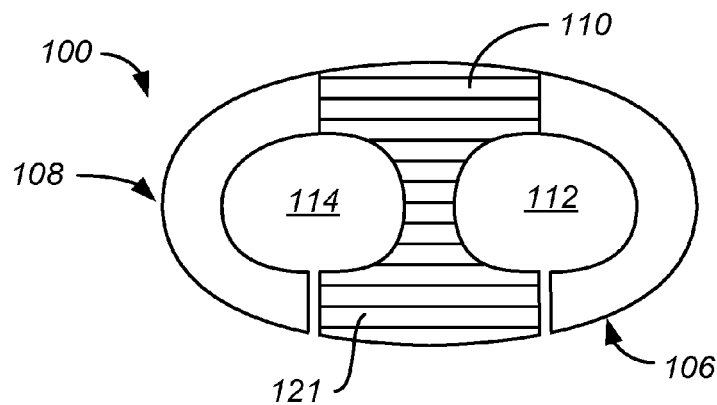

Referring now to FIGS. 5A-5C, dynamic and intervertebral spaces according to present invention may be formed from one or more ring structures, typically joined in a monolithic or integrated geometry. In particular, ring 100 has an anterior portion 102, a posterior portion 104, a right lateral portion 106, and a left lateral portion 108. In addition, a center region 110 is formed between the right lateral portion and left lateral portion, defining a right open region 112 and a left open region 114. One of the gaps 122 opens into the right open region 112 and the other of the gaps 122 opens into the left open region 114. In this way, the center region 110 is "cantilevered" from the posterior region 104 and is free to move in the vertical direction relative to both lateral portions 106 and 108. In the illustrated embodiment, the center region 112 is raised relative to the right and left lateral portions 106 and 108 when unconstrained so that, once implanted, a superior surface 120 of the center region 112 will engage the lower surface of an adjacent, superior vertebral body. Conversely, the inferior surfaces of the both the right lateral portion 106 and left lateral portion 108 will contact the superior surface of the inferior vertebral body. A vertical offset remains between the inferior surface of the center portion 110 and the superior surface of the inferior vertebral body, thus allowing the desired dynamic vertical movement of the vertebral bodies to promote bone growth. The ring 103 will typically include bone attachment screws (not shown), including at least one for each lateral region and one for the center region. Additional, bone attachment regions 116 and 118 will typically be formed on the inferior surfaces of the right lateral portion 106 and left lateral portion 108, as shown in FIG. 5B which is a bottom plan view of the ring 100. In contrast, the inferior surface 120 of the center region 110 will be free from such features as bone attachment is not desired. The bone attachment regions on the superior surface of the ring 100 will be arranged opposite to the arrangement on the inferior surface, i.e. the superior surface 121 of the center portion 110 will have bone attachment features while the superior surfaces of the right lateral portion 106 and left lateral portion 108, as shown in FIG. 5C which is a top plan view of the ring 100, are free from such attachment features.

Figure 6:
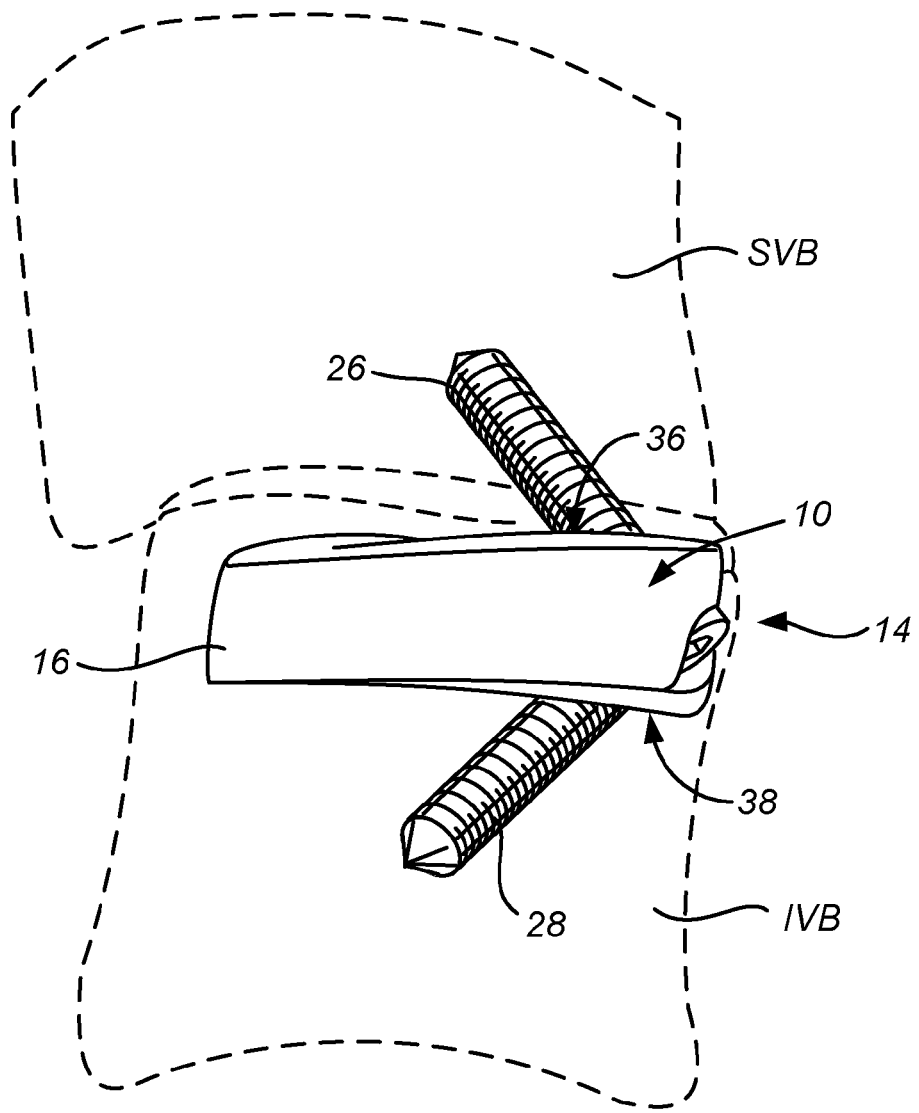
FIG. 6 is a side or lateral view of the dynamic intervertebral spacer of FIGS. 1A and 1B shown implanted between a superior vertebral body and an inferior vertebral body.
Figure 7:
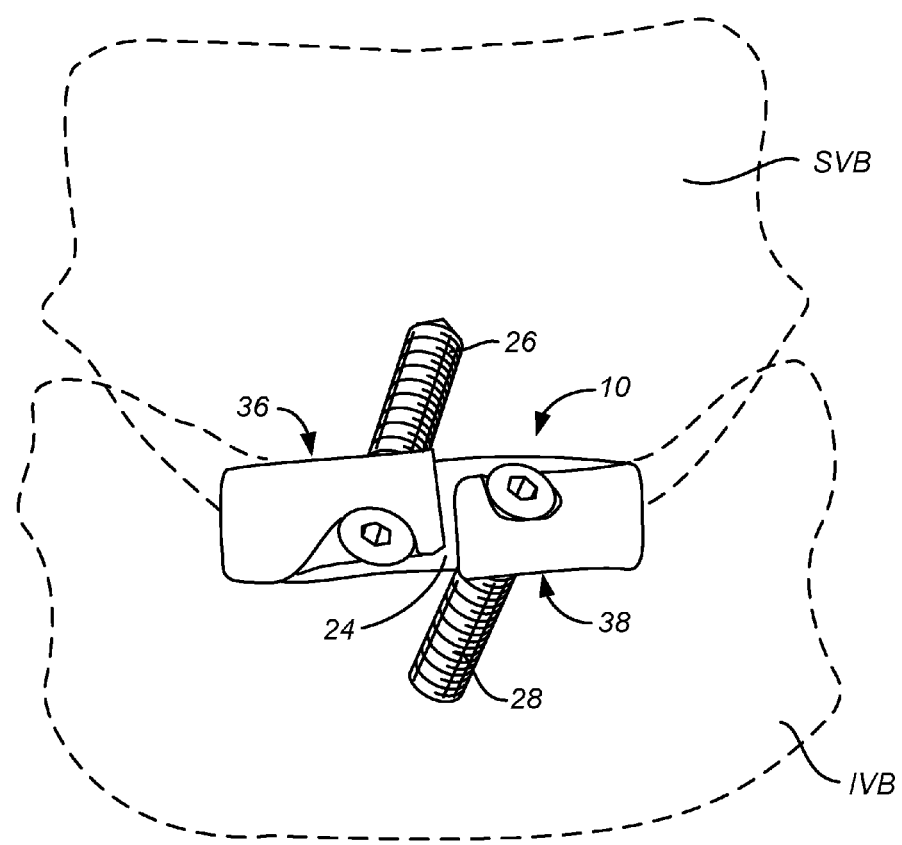
FIG. 7 is a view of the implanted dynamic intervertebral spacer FIG. 6 shown from a front or anterior perspective.

Referring now to FIGS. 6 and 7, implantation of the dynamic spacer 10 of FIGS. 1A, 1B and 2A-2C is illustrated. The posterior portion 14 of the ring 12 is directed toward the patient's posterior while the anterior portion 14 is directed toward the patient's anterior. The gap 24 (best seen in FIG. 7) is thus aligned with the anterior surfaces of the vertebral bodies, allowing movement as the patient's spine experiences flexion and extension.

Figure 8:
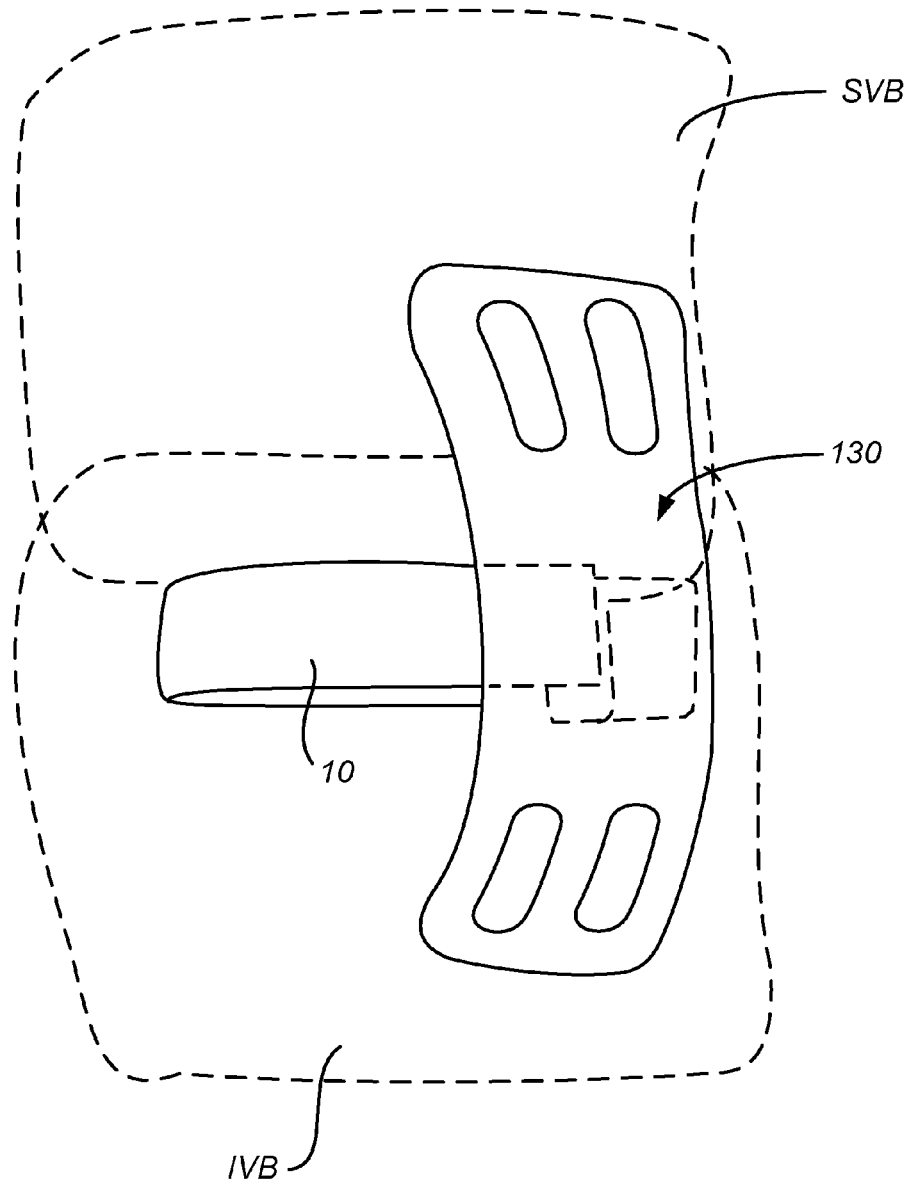
FIG. 8 illustrates the implantation of a dynamic intervertebral spacer in combination with a dynamic bone plate.

Referring now to FIG. 8, the dynamic intervertebral spacers of the present invention may be used in combination with other dynamic vertebral stabilization devices, such as a dynamic bone plate 130 which may be implanted after implantation of the dynamic intervertebral spacer 10.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. A dynamic intervertebral spacer comprising:
   a ring having an anterior portion, a posterior portion, a right lateral portion, a left lateral portion, and an open center portion, wherein said ring is configured to be implanted in a space between adjacent vertebral bodies;
   wherein the ring is split in the anterior portion and superior and inferior surfaces on a right side thereof are vertically offset from superior and inferior surfaces on a left side thereof; and
   wherein the posterior portion of the ring is configured to act as a torsion spring to allow the vertical offset to decrease under load on the superior and inferior surfaces of the ring.

2. A spacer as in claim 1, wherein one of the superior and inferior surfaces on the right side of the ring is configured to provide attachment to an adjacent vertebral body and the other of the superior and inferior surfaces on the left side of the ring is configured to provide attachment to another adjacent vertebral body.

3. A spacer as in claim 2, wherein the surfaces have surface features or coatings which promote bone ingrowth.

4. A spacer as in claim 2, wherein the right and left sides of the ring each have at least one bone screw, wherein the bone screw(s) on one side are configured to attach to a posterior vertebral body and the bone screw(s) on the another side are configured to attach to an inferior vertebral body.

5. A spacer as in claim 1, wherein the ring has right and left opposed faces at the split.

6. A spacer as in claim 5, wherein the opposed faces are planar.

7. A spacer as in claim 5, where in the opposed faces are non-planar.

8. A spacer as in claim 7, wherein the non-planar faces define a path of separation which is non-linear in a superior-to-inferior direction.

9. A spacer as in claim 8, wherein the non-planar faces define a path of separation which is non-linear in an anterior-to-posterior direction.

10. A spacer as in claim 1, wherein the ring consists of a monolithic body.

11. A spacer as in claim 10, wherein the monolithic body consists of a polymer.

12. A spacer as in claim 11, wherein the polymer is selected from the group consisting of polyether ether ketones (PEEK), polyaryl ether ketones (PAEK), and their composites, such as carbon fiber reinforced or with radiopaque compounds.

13. A spacer as in claim 10, wherein the monolithic body consists of a metal.

14. A spacer as in claim 13, wherein the metal is selected from the group consisting of titanium, and its alloys such as nitinol, cobalt chrome molybdenum and variants.

15. A spacer as in claim 1, wherein the vertical offset is in the range from 0.05 mm to 3.0 mm.

16. A spacer as in claim 5, wherein the vertical offset resists the compression with a spring force in the range from 20 N/mm to 40000 N/mm.

17. A spacer as in claim 1, wherein the superior surface has a convex geometry.

18. A method for dynamically fusing adjacent vertebral bodies in a patient's spine,
   implanting a spacer between the adjacent vertebral bodies; and
   filling a center of the spacer with a bone graft material;
   wherein superior and inferior surfaces on a right side of an anterior portion of the spacer are vertically offset from superior and inferior surfaces on a left side of the anterior portion and the vertical offset elastically resists flexion to promote bone growth.

19. A method as in claim 18, wherein the vertical offset resists flexion with an elastic constant in the range from 20 N/mm to 40000 N/mm.

20. A method as in claim 18, wherein there is a gap between the superior surface and the adjacent vertebral body on one side of the spacer and a gap between the inferior surface and the other adjacent vertebral body on the other side of the spacers, wherein the gaps allow the elastic resistance to flexion.

21. A method as in claim 20, further comprising promoting bone ingrowth on the spacer surfaces which are in contact with the adjacent vertebral bodies when the vertebral bodies are not in flexion.

22. A method as in claim 20, further comprising screwing the inferior surface of the one side of the spacer into the other adjacent vertebral body and screwing the superior surface of the other side of the spacer into the adjacent vertebral body.

* * * * *